United States Patent
Hirose

(10) Patent No.: US 11,716,532 B2
(45) Date of Patent: Aug. 1, 2023

(54) CONTROL APPARATUS AND MEDICAL OBSERVATION SYSTEM

(71) Applicant: Sony Olympus Medical Solutions Inc., Tokyo (JP)

(72) Inventor: Kenji Hirose, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 17/176,186

(22) Filed: Feb. 16, 2021

(65) Prior Publication Data

US 2021/0297576 A1  Sep. 23, 2021

(30) Foreign Application Priority Data

Mar. 17, 2020 (JP) .............................. JP2020-046854
Dec. 15, 2020 (JP) .............................. JP2020-207970

(51) Int. Cl.
| | |
|---|---|
| *G02B 15/16* | (2006.01) |
| *H04N 23/66* | (2023.01) |
| *G06F 3/16* | (2006.01) |
| *G02B 21/00* | (2006.01) |
| *G02B 21/24* | (2006.01) |
| *A61B 90/00* | (2016.01) |
| *G02B 21/36* | (2006.01) |
| *H04N 23/959* | (2023.01) |
| *G02B 30/22* | (2020.01) |

(52) U.S. Cl.
CPC ........... *H04N 23/66* (2023.01); *A61B 90/361* (2016.02); *A61B 90/37* (2016.02); *G02B 21/0012* (2013.01); *G02B 21/241* (2013.01); *G02B 21/365* (2013.01); *G06F 3/167* (2013.01); *H04N 23/959* (2023.01); *G02B 30/22* (2020.01)

(58) Field of Classification Search
CPC .......... H04N 5/23203; H04N 5/232125; A61B 90/361; A61B 90/37; G02B 21/0012; G02B 21/241; G02B 21/365; G02B 30/22; G06F 3/167
See application file for complete search history.

(56) References Cited

U.S. PATENT DOCUMENTS

| | | | | |
|---|---|---|---|---|
| 4,989,253 | A * | 1/1991 | Liang .................. | G02B 21/0012 704/E15.045 |
| 2015/0181107 | A1* | 6/2015 | Park .................. | H04N 5/232123 348/353 |
| 2015/0244929 | A1* | 8/2015 | Lee .................. | H04N 5/232125 348/346 |
| 2017/0359536 | A1* | 12/2017 | Lee ......................... | H04N 5/144 |
| 2018/0368656 | A1* | 12/2018 | Austin .................... | A61B 1/051 |
| 2019/0392831 | A1* | 12/2019 | Pohl ...................... | G06N 3/0454 |

FOREIGN PATENT DOCUMENTS

| | | |
|---|---|---|
| JP | 2001-175281 A | 6/2001 |
| JP | 2016-42982 A | 4/2016 |

* cited by examiner

*Primary Examiner* — Patrick E Demosky
(74) *Attorney, Agent, or Firm* — Xsensus LLP

(57) ABSTRACT

A control apparatus includes: an acquisition unit configured to acquire an operation instruction made by a voice input to an imaging device including: an optical system including a focus lens; and an image sensor; and a controller configured to control the focus lens moving at a first velocity to stop movement when the operation instruction is an instruction to stop an operation of the focus lens, and control the focus lens to move at a second velocity lower than the first velocity.

15 Claims, 10 Drawing Sheets

CONTROL APPARATUS AND MEDICAL OBSERVATION SYSTEM

CROSS-REFERENCE TO RELATED APPLICATIONS

This application claims priority from Japanese Application No. 2020-046854, filed on Mar. 17, 2020, and Japanese Application No. 2020-207970, filed on Dec. 15, 2020, the entire contents of each are incorporated herein by its reference.

BACKGROUND

The present disclosure relates to a control apparatus and a medical observation system.

There is known a medical observation system that magnifies and performs imaging of a surgical site when performing surgery on the brain, heart, or the like, of a patient as an observation target, and displays the captured image on a monitor (refer to JP 2016-42982 A, for example). In this medical observation system, a microscope apparatus has a focus function.

When a user such as a doctor uses the focus function to bring an image in focus, the user needs to operate a predetermined switch. During this operation, the user has to interrupt the surgery or change his/her posture, which is considered to be far from being efficient. To overcome this problem, it is conceivable that the user performs various operations by inputting voice.

However, in the case of voice input, there would be requirements for the time, specifically, the time for the user to utter, the time for transmitting a voice signal to the control apparatus, the time for the control apparatus to recognize an instruction in the utterance, and the time for completing the operation. Due to these requirements, there would be a delay from the timing of the user utterance. Because of this delay, when the user attempts focusing using voice input, the focus lens would not stop at a position intended by the user, leading to a failure in the focusing.

To handle this, it is conceivable to employ a technique that achieves the processing intended by the user in consideration of the time difference between operation command timing intended by the user and operation command timing actually given by the user (for example, refer to JP 2001-175281 A).

SUMMARY

The above-described technique of JP 2001-175281 A has a problem of an increased load on the system due to complicated processes.

There is a need for a control apparatus and a medical observation system achieving focus adjustment using voice input by a simple process with less load.

According to one aspect of the present disclosure, there is provided a control apparatus including: an acquisition unit configured to acquire an operation instruction made by a voice input to an imaging device including: an optical system including a focus lens; and an image sensor; and a controller configured to control the focus lens moving at a first velocity to stop movement when the operation instruction is an instruction to stop an operation of the focus lens, and control the focus lens to move at a second velocity lower than the first velocity.

DETAILED DESCRIPTION

Hereinafter, embodiments (hereinafter, referred to as embodiments) will be described with reference to the attached drawings.

First Embodiment

Figure 1:
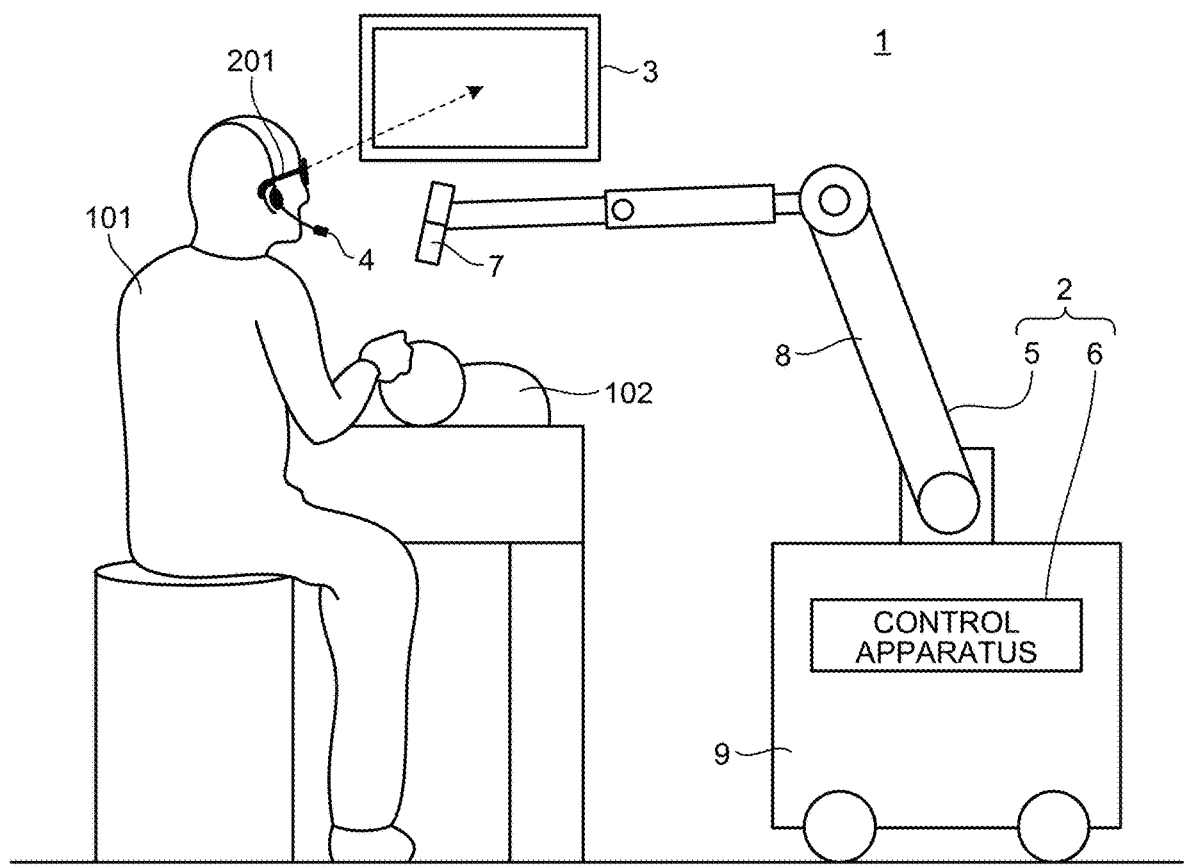
FIG. 1 is a diagram schematically illustrating a medical observation system according to a first embodiment.

FIG. 1 is a diagram schematically illustrating a medical observation system according to a first embodiment. FIG. 1 illustrates a situation in which a user 101 such as a doctor who performs a surgery using a medical observation system 1 is performing surgery of the head of a patient 102. The medical observation system 1 illustrated in FIG. 1 includes a medical observation apparatus 2, a display device 3, and a microphone 4.

The medical observation apparatus 2 is a surgical microscope, and includes a microscope apparatus 5 and a control apparatus 6. The microscope apparatus 5 has a function as an imaging device that performs imaging of an observation target and generates an image signal.

Having a wireless or wired connection with the control apparatus 6, the display device 3 receives a three-dimensional image signal or a two-dimensional image signal from the control apparatus 6, and displays a three-dimensional image (3D image) based on the three-dimensional image signal or a two-dimensional image (2D image) based on the two-dimensional image signal. The display device 3 includes a display panel formed with liquid crystal, organic electro luminescence (EL), or the like. The display device 3 displays an image of the surgical site of the patient 102 captured in the imaging by the microscope apparatus 5. FIG. 1 schematically illustrates a situation in which the user 101 wearing 3D glasses 201 is visually observing a 3D image, which is displayed on the display device 3.

Having a wireless or wired connection with the control apparatus 6, the microphone 4 receives a voice input of the user 101, generates a voice signal, and transmits the generated voice signal to the control apparatus 6.

A visual configuration of the microscope apparatus 5 will be described. The microscope apparatus 5 includes a microscope unit 7 that magnifies and performs imaging of a microstructure of an observation target, a support 8 that supports the microscope unit 7, and a base 9 that holds a proximal end of the support 8 while incorporating the control apparatus 6.

The microscope unit 7 has a tubular portion having a columnar shape. On an aperture surface at a lower end of a main body, a cover slip is provided (not illustrated). The tubular portion has a size graspable by the user, and movable by the user while being grasped by the user when an imaging field of view of the microscope unit 7 is changed by the user. The shape of the tubular portion is not limited to the cylindrical shape, and may be a polygonal tubular shape.

The support 8 has a plurality of links on an arm unit, and the adjacent links are pivotably connected to each other via joint portions. The support 8 includes, within an internal hollow portion, a transmission cable to transmit various signals between the microscope unit 7 and the control apparatus 6, and a light guide to transmit illumination light generated by the control apparatus 6 to the microscope unit 7.

The control apparatus 6 acquires a voice signal generated by the microphone 4 and recognizes information carried by the voice signal. For example, expressions instructing the focus operation of the microscope apparatus 5 are "focus in" or "focus out", while an expression of stopping the focus operation of the microscope apparatus 5 is "stop". At execution of focus operation of the microscope apparatus 5, the control apparatus 6 first controls to stop a focus lens 511 (described below) of the microscope apparatus 5 in response to a voice input, and thereafter controls to move the focus lens at a constant velocity of a second velocity that is lower than and in an opposite direction of a first velocity at a time of constant velocity movement before the stoppage of the focus lens 511. Needless to say, the velocity changes before and after the constant velocity movement. In addition, a period of the constant velocity movement contains a slight change in velocity of about several percent with respect to the constant velocity. The above expressions used at voice instruction of the focus operation are only an example, and other expressions may be used.

Figure 2A:
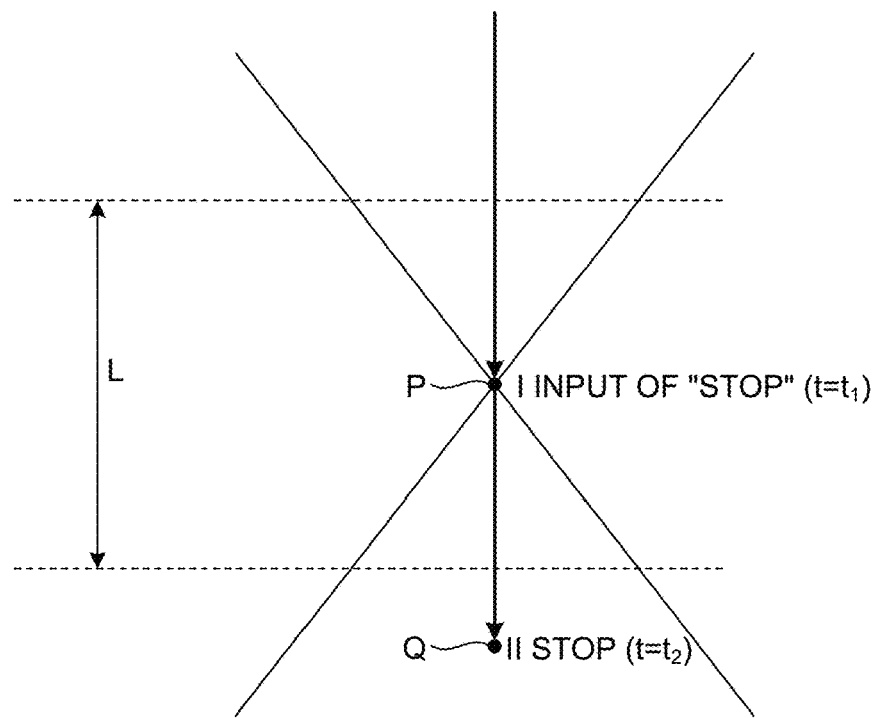
FIG. 2A is a diagram (part 1) schematically illustrating a focus operation according to the first embodiment.
Figure 2B:
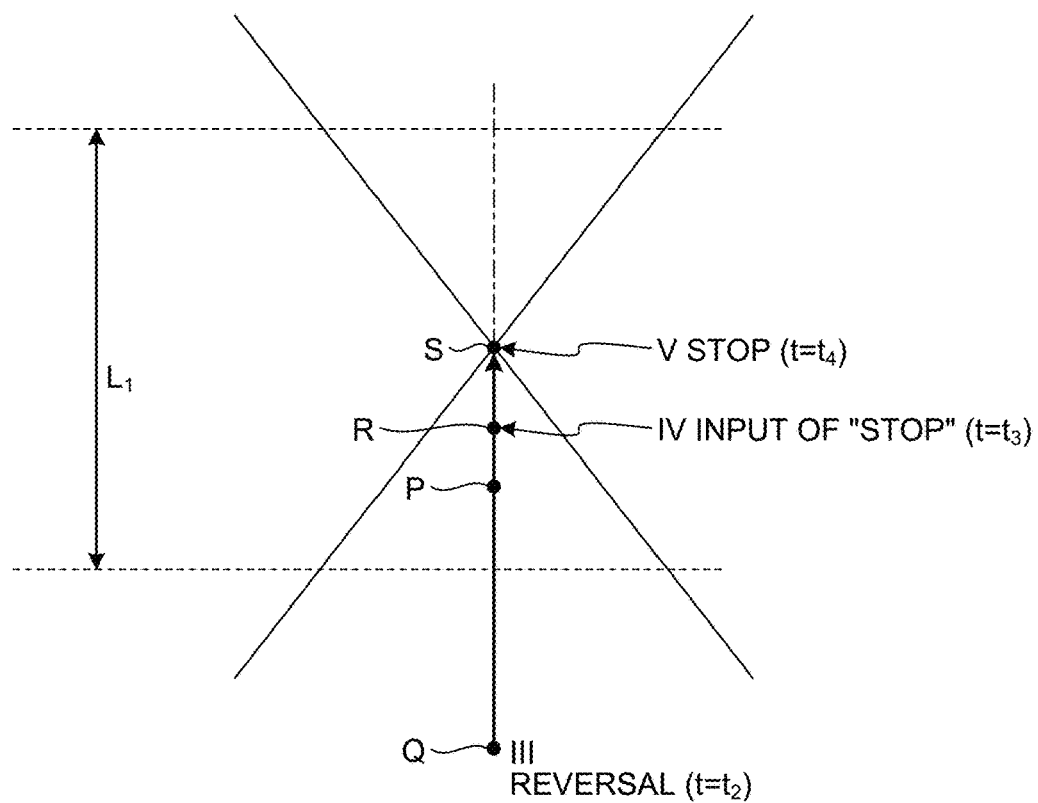
FIG. 2B is a diagram (part 2) schematically illustrating the focus operation according to the first embodiment.

FIGS. 2A and 2B are diagrams schematically illustrating the focus operation in the first embodiment. FIG. 2A schematically illustrates a movement of a focus position of the focus lens 511 until the focus operation is stopped. FIG. 2B schematically illustrates a movement of the focus position of the focus lens 511 to return in the opposite direction after the focus operation is stopped.

First, FIG. 2A will be described. To stop the focus operation, the user 101 utters "stop" to allow this utterance to be input to the microphone 4. FIG. 2A illustrates a case where a focus position as a desirable targeted focus position at which the focus lens 511 is to be stopped is defined as a target position P, and the user 101 utters "stop" at time $t=t_1$ at the timing when the focus position of the focus lens 511 is located at the target position P. After recognizing the voice signal acquired from the microphone 4, the control apparatus 6 transmits a control signal instructing the microscope apparatus 5 to stop the focus operation. This produces a time difference between the "stop" input timing (I) by the user 101 and the stop timing (II) of the focus lens 511, and thus, a focus position (hereinafter, referred to as a "stop position") Q at which the focus lens 511 stops overruns from the target position P by the amount of time difference. FIG. 2A illustrates a situation in which the stop position Q at the time when the focus lens 511 stops at time $t=t_2$ is located outside a depth of focus (depth L) when the focus position of the focus lens 511 is located at the target position P. In this case, the display device 3 displays an image that is out of focus.

Next, FIG. 2B will be described. Immediately after stopping at the time when the focus position is at the stop position Q, the focus lens 511 reverses the direction and begins to return so that the focus position is directed toward the target position P (III). Thereafter, at the time $t=t_3$ when the focus position of the focus lens 511 passes through a return position R, the user utters "stop" and inputs the utterance to the microphone 4 (IV). Thereafter, the focus lens 511 gradually decelerates and stops at the time $t=t_4$. The focus position of the focus lens 511 at this time is a stop position S near the target position P (V). The target position P is located within a depth of focus (depth $L_1$) of the focus lens 511 when the focus position is at the stop position S. Although FIG. 2B illustrates a case where the focus lens 511 stops after the passage of the focus position of the focus lens 511 through the target position P again, the focus lens 511 stops in some cases without the passage of the focus position of the focus lens 511 through the target position P again depending on the voice input timing of the user.

When the depths L and $L_1$ of the two depths of focus described above are equal, and when the stop position S is located within the depth of focus when the focus position is located at the target position P (FIG. 2A), effects similar to the case illustrated in FIG. 2B will be obtained.

Figure 3:
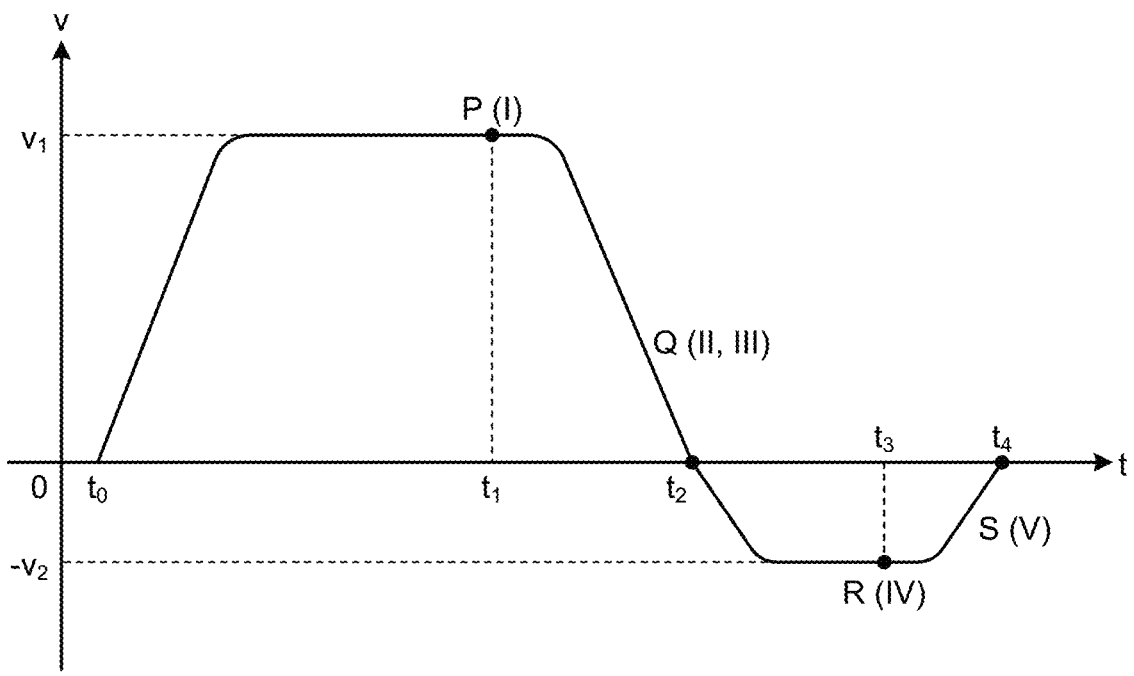
FIG. 3 is a diagram illustrating a relationship between the time and velocity during the focus operation illustrated in FIGS. 2A and 2B.

FIG. 3 is a diagram illustrating a relationship between the time and the velocity during the focus operation illustrated in FIGS. 2A and 2B, specifically illustrating a relationship between the time and the velocity when the focus operation is started at the time $t=0$. The user makes a voice input of "focus in" or "focus out" to the microphone 4 at $t=0$, and then the focus lens 511 starts moving at time $t=t_0$ with a slight delay from the voice input, and eventually shifts to a constant velocity movement at a first velocity $v_1$. The user makes a voice input of "stop" to the microphone 4 at time $t=t_1$ on which the focus position of the focus lens 511 passes through the target position P (I), the focus lens 511 starts decelerating with a slight delay from the voice input, and stops at time $t=t_2$. The focus position of the focus lens 511 at this time is the stop position Q (II). Immediately after that, the focus lens 511 reverses and starts moving in the opposite direction (III), and eventually shifts to a constant velocity movement at a second velocity $v_2$, which is lower than the first velocity $v_1$. This second velocity $v_2$ is a velocity capable of stopping within the depth of focus of a lens unit 51. Thereafter, the user makes a voice input of "stop" again to the microphone 4 at time $t=t_3$ on which the focus position of the focus lens 511 passes through the return position R (IV), the focus lens 511 starts decelerating with a slight delay from the voice input, and stops at time $t=t_4$. The focus position of the focus lens 511 at this time is the stop position S (V).

Note that the expressions ("focus in", "focus out", "stop") corresponding to the various operation instructions described above are merely examples, and other expressions may be adopted.

Figure 4:
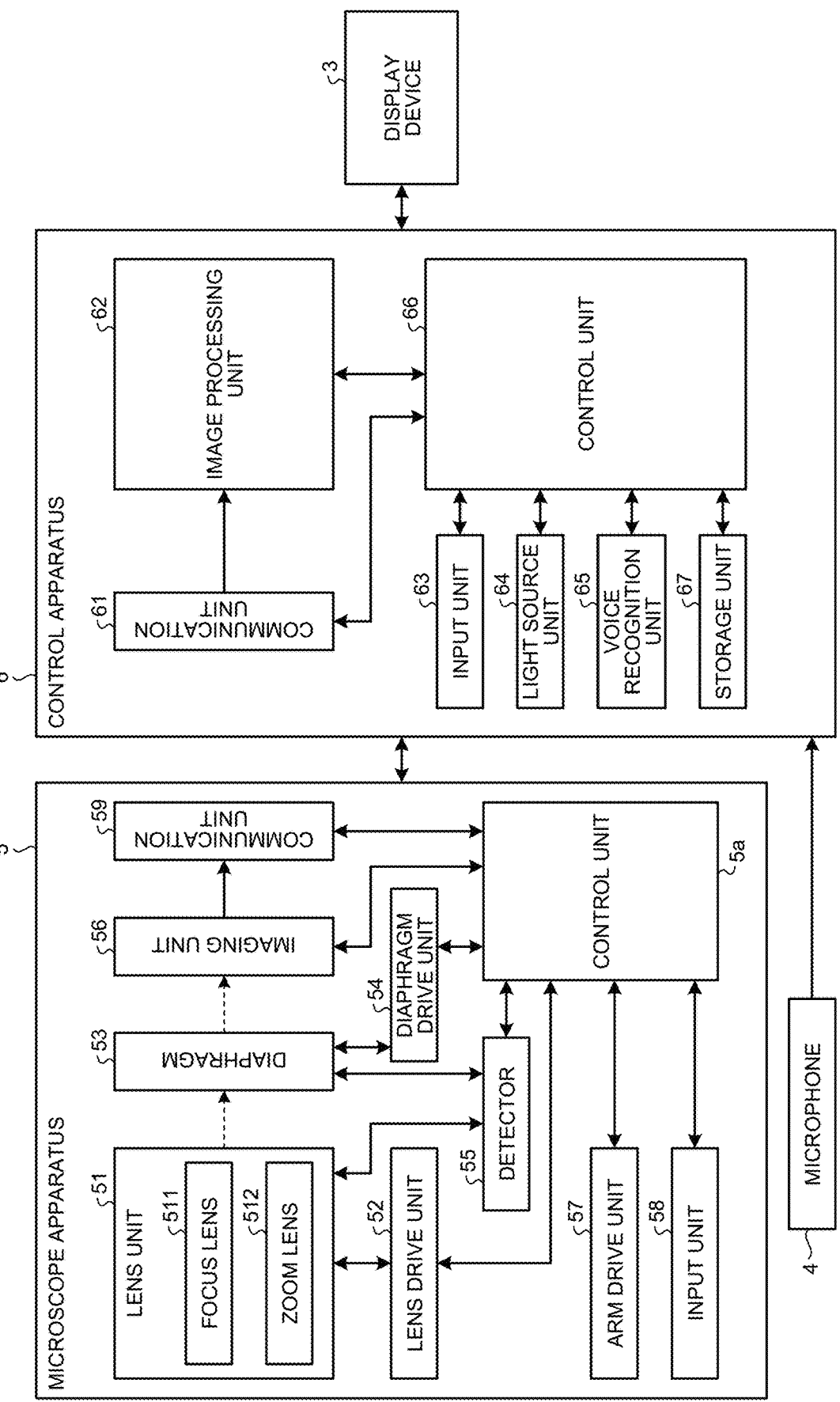
FIG. 4 is a block diagram illustrating a functional configuration of the medical observation system according to the first embodiment.

FIG. 4 is a block diagram illustrating the functional configuration of the medical observation system 1. First, the functional configuration of the microscope apparatus 5 will be described. The microscope apparatus 5 includes a lens unit 51, a lens drive unit 52, a diaphragm 53, a diaphragm drive unit 54, a detector 55, an imaging unit 56, an arm drive unit 57, an input unit 58, a communication unit 59, and a control unit 5a.

The lens unit 51 is an optical system that includes a plurality of lenses movable along an optical axis and that forms a condensed subject image on an imaging surface of an image sensor included in the imaging unit 56. The lens unit 51 includes a focus lens 511 that adjusts the focus and a zoom lens 512 that changes the angle of view. The focus lens 511 and the zoom lens 512 each include one or more lenses.

The lens drive unit 52 includes: an actuator that moves the focus lens 511 and the zoom lens 512 individually; and a driver that drives the actuator under the control of the control unit 5a.

The diaphragm 53 is provided between the lens unit 51 and the imaging unit 56, and adjusts the amount of light for the subject image from the lens unit 51 toward the imaging unit 56 under the control of the control unit 5a. The diaphragm 53, together with the lens unit 51, constitutes the optical system of the microscope apparatus 5.

The diaphragm drive unit 54 operates the diaphragm 53 under the control of the control unit 5a to adjust an aperture value (also referred to as an F-number).

The detector 55 includes two position sensors that detect the positions of the focus lens 511 and the zoom lens 512 individually, and an encoder that detects the aperture value of the diaphragm 53. The detector 55 outputs the detected position of the zoom lens 512 and the aperture value of the diaphragm 53 to the control unit 5a.

The imaging unit 56 includes: an image sensor that forms an image from the subject image condensed by the lens unit 51 to generate a captured image (analog signal); and a signal processing unit that performs signal processing such as noise reduction or A/D conversion on the image signal (analog signal) from the image sensor. The image sensor is formed with a complementary metal oxide semiconductor (CMOS) image sensor or a charge coupled device (CCD) image sensor, or the like. The imaging unit 56 may have two image sensors. In this case, the imaging unit 56 may generate a three-dimensional image (3D image).

The arm drive unit 57 allows a plurality of joints of the support 8 to operate under the control of the control unit 5a. Specifically, the arm drive unit 57 includes: an actuator provided at a joint portion between the arms; and a driver to drive the actuator.

The input unit 58 receives inputs such as an operation signal of the lens unit 51 and an arm operation signal for the support 8. The input unit 58 has a plurality of switches, buttons, or the like provided at positions on the side surface of the tubular portion of the microscope unit 7 where the user may perform operation while holding the microscope unit 7.

The communication unit 59 is an interface for communicating with the control apparatus 6. The communication unit 59 transmits an image signal (digital signal) generated by the imaging unit 56 to the control apparatus 6, and also receives a control signal from the control apparatus 6.

The control unit 5a controls the operation of the microscope apparatus 5 in cooperation with a control unit 66 of the control apparatus 6. The control unit 5a controls the microscope apparatus 5 to operate based on an operation instruction signal that the input unit 58 receives the input and the operation instruction signal transmitted from the control unit 66 of the control apparatus 6. In the present embodiment, a signal for allowing operation of the arm to move the imaging field of view of the microscope apparatus 5 is received from the control unit 66 of the control apparatus 6.

The control unit 5a includes at least one processor such as a central processing unit (CPU), a field programmable gate array (FPGA), and an application specific integrated circuit (ASIC).

Next, the functional configuration of the control apparatus 6 will be described. The control apparatus 6 includes a communication unit 61, an image processing unit 62, an input unit 63, a light source unit 64, a voice recognition unit 65, a control unit 66, and a storage unit 67. The communication unit 61 acquires an image signal obtained in the imaging performed by the microscope apparatus 5 and transmitted via a transmission cable. The image signal includes information related to imaging, such as a gain adjustment value at the time of imaging, a focus lens position, a zoom lens position, a shutter speed, and an aperture value. Furthermore, the communication unit 61 acquires the voice signal of the user 101 an input of which has been received by the microphone 4, as an operation instruction. In this sense, the communication unit 61 has a function of an acquisition unit.

The image processing unit 62 performs various signal processing on the image signal acquired by the communication unit 61 and thereby generates an image signal for display, and outputs the generated image signal to the display device 3. Specific examples of image processing include known image processing such as a detection process of brightness level and contrast of an image signal, gain adjustment, interpolation processing, color correction processing, color enhancement processing, and contour enhancement processing. The image processing unit 62 includes at least one of the processors such as a CPU, an FPGA, and an ASIC.

The input unit 63 receives inputs of various types of information. The input unit 63 is implemented by using a user interface such as a keyboard, a mouse, a touch panel, or a foot switch. The input unit 63 may have at least a part of the functions of the input unit 58 of the microscope apparatus 5.

The light source unit 64 generates illumination light to be supplied to the microscope apparatus 5 via a light guide. The light source unit 64 includes a solid-state light emitting element such as a light emitting diode (LED) or a laser diode (LD), a laser light source, a xenon lamp, a halogen lamp, or the like.

The voice recognition unit 65 executes a recognition process on the voice signal received from the microphone 4. By comparing the feature data of the voice signal with the feature data stored in the storage unit 67, the voice recognition unit 65 recognizes information carried by the voice signal.

The control unit 66 controls the operation of the control apparatus 6 as well as performing comprehensive control of the operation of the medical observation apparatus 2 in cooperation with the control unit 5a of the microscope apparatus 5. The control unit 66 generates a control signal for operating the microscope apparatus 5 based on the information carried by the voice signal recognized by the voice recognition unit 65, and transmits the generated control signal to the microscope apparatus 5. When information carried by the voice signal recognized by the voice recognition unit 65 is an instruction to stop the operation of the focus lens 511, the control unit 66 first controls to stop the focus lens 511 and thereafter controls to move the focus lens 511 at a constant velocity of the second velocity lower than the first velocity at the time of constant velocity movement before the stoppage of the focus lens 511. In order to set a brightness level of the image signal obtained by imaging by the microscope apparatus 5 to a predetermined brightness level, the control unit 66 performs control such as the shutter speed of the imaging unit 56, a gain adjustment performed by the image processing unit 62, and the amount of illumination light generated by the light source unit 64. Furthermore, the control unit 66 controls the display of the display device 3. The first velocity and the second velocity do not have to be the velocity at the time of the constant velocity movement, and may be, a typical velocity, for example. The typical velocity may be determined at a predetermined timing or position, may be the average velocity during movement, or may be the velocity that continues for the longest time.

The control unit 66 includes at least one of processors such as a CPU, an FPGA, and an ASIC. The image processing unit 62 and the control unit 66 may use one processor as a common processor.

The storage unit 67 stores the first velocity $v_1$ and the second velocity $v_2$ during the focus operation. The storage unit 67 stores various programs needed for operation of the control apparatus 6, and temporarily stores the data under arithmetic processing performed by the control apparatus 6. The storage unit 67 includes random access memory (RAM), read only memory (ROM), or the like.

Figure 5:
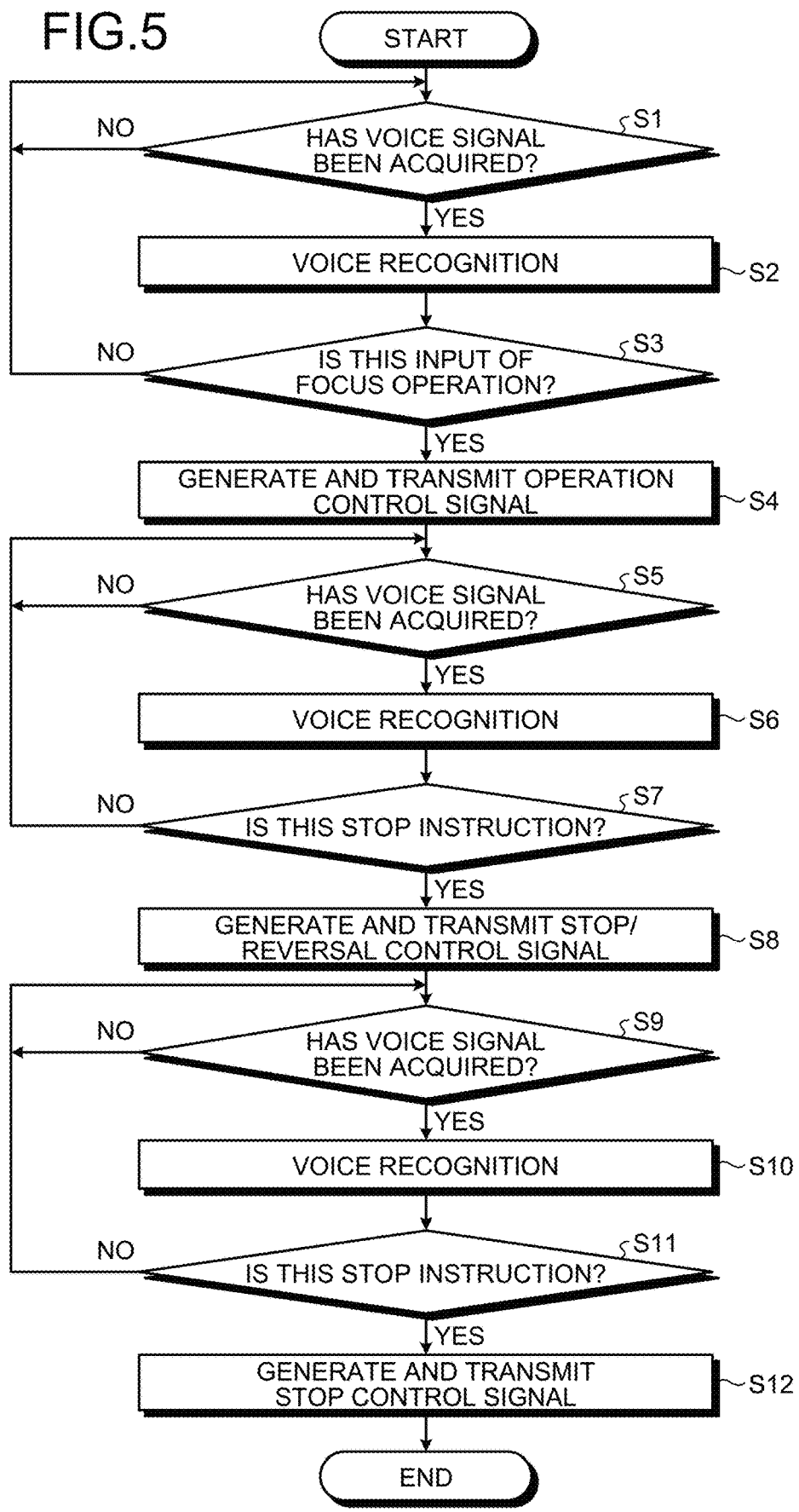
FIG. 5 is a flowchart illustrating an outline of processes performed by a control apparatus according to the first embodiment.

FIG. 5 is a flowchart illustrating an outline of processing performed by the control apparatus 6. In parallel with the processes described below, the control apparatus 6 performs processes in which the communication unit 61 sequentially acquires image data captured by the imaging unit 56 from the microscope apparatus 5, and the image processing unit 62 generates an image signal for display and outputs the generated image signal to the display device 3. The execution of these processes is common to all the flowcharts described below.

First, after the communication unit 61 acquires a voice signal (step S1: Yes), the voice recognition unit 65 performs a voice signal recognition process (step S2). When the communication unit 61 has not acquired the voice signal in step S1 (step S1: No), the control apparatus 6 repeats step S1.

When it is determined, as a result of the recognition process, that the voice input is an input of focus operation (for example, "focus in" or "focus out") (step S3: Yes), the control unit 66 generates a control signal (operation control signal) that controls to operate the lens drive unit 52 of the microscope apparatus 5 and transmits the generated control signal to the control unit 5*a* (step S4). This causes the lens drive unit 52 to move the focus lens 511 under the control of the control unit 5*a*. The temporal change of the velocity of the focus lens 511 is illustrated in FIG. 3, for example, and includes a constant velocity movement at the first velocity $v_1$ on the way. When it is determined, as a result of the recognition process, that the voice input is not an input of focus operation (step S3: No), the control apparatus 6 returns to step S1.

After step S4, when the communication unit 61 acquires a voice signal (step S5: Yes), the voice recognition unit 65 performs a recognition process on the voice signal (step S6). When the communication unit 61 has not acquired the voice signal in step S5 (step S5: No), the control apparatus 6 repeats step S5. When the communication unit 61 has not acquired a voice signal even when a predetermined time has elapsed after step S4, the control unit 66 may display information prompting the user 101 to perform a voice input, on the display device 3. Furthermore, the control unit 66 may output from the speaker a message or an alarm sound prompting the user 101 to perform a voice input.

When it is determined, as a result of the recognition process in step S6, that the voice input is a focus operation stop instruction (for example, "stop") (step S7: Yes), the control unit 66 generates a control signal (stop/reverse control signal) to stop the operation of the lens drive unit 52 and reverses the direction, and transmits the generated control signal to the control unit 5*a* (step S8). This causes the lens drive unit 52 to stop the focus lens 511 and thereafter reverses and moves the focus lens 511 under the control of the control unit 5*a*. The temporal change of the velocity of the focus lens 511 at the reversal is illustrated in FIG. 3 ($t\ t_2$), for example, and includes a constant velocity movement at the second velocity $v_2 (< v_1)$ on the way.

When it is determined, as a result of the recognition process in step S6, that the voice input is not a focus operation stop instruction (step S7: No), the control apparatus 6 returns to step S5. When no focus operation stop instruction has been input even when a predetermined time has elapsed after step S4, the control unit 66 may display information prompting the user 101 to perform a voice input, on the display device 3. Here, the control unit 66 may also output a message or an alarm sound prompting the user 101 to perform a voice input from a separately installed speaker.

After step S8, when the communication unit 61 has acquired a voice signal (step S9: Yes), the voice recognition unit 65 performs a recognition process on the voice signal (step S10). When the communication unit 61 has not acquired any voice signal in step S9 (step S9: No), the control apparatus 6 repeats step S9.

When it is determined, as a result of the recognition process in step S10, that the voice input is a focus operation stop instruction (for example, "stop") (step S11: Yes), the control unit 66 generates a control signal (stop control signal) to stop the operation of the lens drive unit 52, and transmits the generated control signal to the control unit 5*a* (step S12). This causes the lens drive unit 52 to stop the focus lens 511 under the control of the control unit 5*a*. This completes a series of the operations of the control apparatus 6.

When it is determined, as a result of the recognition process in step S10, that the input is not a focus operation stop instruction (step S11: No), the control apparatus 6 returns to step S9.

According to the first embodiment described above, recognition is performed on information carried by the voice signal acquired from the microphone that receives a voice input of an operator of the imaging device equipped with the optical system including the focus lens and the imaging unit. When the recognized information is an instruction to stop the operation of the focus lens, the focus lens will be stopped and thereafter the focus lens will be moved at a constant velocity of the second velocity that is lower than and in an opposite direction of the first velocity at a time of constant velocity movement before the stoppage of the focus lens. This makes it possible to perform focus adjustment just by using voice input. Therefore, the focus adjustment by voice input may be achieved by a simple process with less load.

Furthermore, according to the first embodiment, even when a delay from the voice input occurs, fine adjustment may be performed by the voice input alone, making it possible to facilitate the focus adjustment.

Furthermore, according to the first embodiment, since the focus lens slowly approaches the target position after the reversal of the lens direction, the user may easily focus while viewing the display device 3.

Furthermore, according to the first embodiment, the focus lens moves at a relatively high velocity before the first stop, and the movement after the reversal of the lens direction is slower than before the stoppage of the focus lens. This makes it possible to reduce the adjustment time compared to the case where the focus lens continuously moves at a lower velocity.

First Modification

A first modification of the first embodiment will be described. In the first modification, the control unit 66 sets the second velocity $v_2$ based on the depth of focus according to the imaging conditions of the microscope apparatus 5 at the time of imaging. Examples of the imaging conditions are include the magnification and/or the aperture value of the diaphragm 53 according to the positions of the focus lens 511 and the zoom lens 512. These values are detected by the detector 55.

The storage unit 67 stores a table that gives a relationship between the depth of focus which is determined in accordance with the magnification and/or the aperture value detected by the detector 55, and the second velocity $v_2$. This relationship is a relationship in which, for example, the shallower the depth of focus, the lower the second velocity $v_2$.

In this modification, in step S8 described above, the control unit 66 first sets the second velocity $v_2$ with reference to the table stored in the storage unit 67, and thereafter generates a control signal that stops the operation of the lens drive unit 52 and performs reversal operation, and transmits the generated control signal to the control unit 5a.

According to the first modification of the first embodiment described above, the control may be performed in accordance with the depth of focus that changes with the imaging conditions.

Second Embodiment

In the second embodiment, after the focus lens is stopped, the focus lens is moved at a third velocity having a direction opposite to the direction of the first velocity and higher than the second velocity for a predetermined time, and thereafter the velocity is reduced to the second velocity having a direction opposite to the direction of the first velocity, and the focus lens is moved at this second velocity. The functional configuration of the medical observation system according to the second embodiment is the similar to that of the first embodiment.

Figure 6:
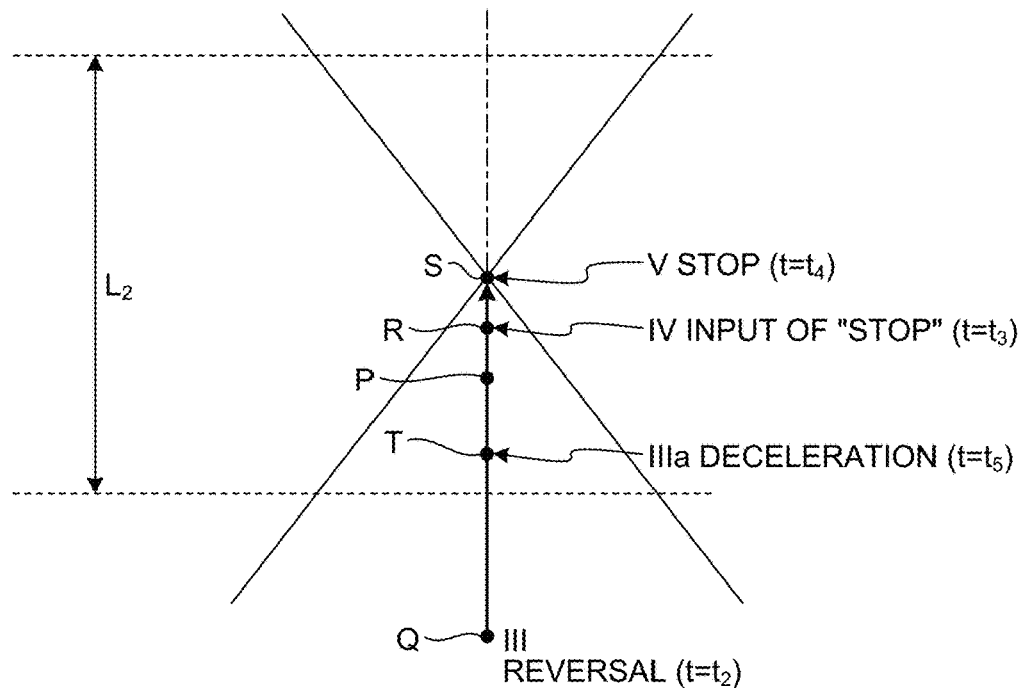
FIG. 6 is a diagram schematically illustrating a movement in which a focus position of a focus lens returns in an opposite direction after the focus operation is stopped in a second embodiment.

FIG. 6 is a diagram schematically illustrating a movement in which the focus position of the focus lens 511 returns in the opposite direction after the focus operation is stopped in the second embodiment. Note that the movement from the start to the stop of the focus operation is the same as that described with reference to FIG. 2A in the first embodiment.

Immediately after stopping at the time when the focus position is at the stop position Q ($t=t_2$), the focus lens 511 reverses the direction and begins to return so that the focus position is directed toward the target position P (III). Thereafter, the focus lens 511 moves at a constant velocity of a third velocity $v_3$, which is higher than the second velocity $v_2$, and then the velocity of the focus lens 511 is decelerated to the second velocity $v_2$ at the time $t=t_5$ at which the focus position passes through the return position T (IIIa). The time $t_5-t_2$ from the start of reversal to the changeover to the second velocity $v_2$ is preset as a time that cancels the delay caused by the processes on the device side after the user's voice input. Subsequently, at the time $t=t_3$ when the focus position of the focus lens 511 passes through a return position R, the user utters "stop" and inputs the utterance to the microphone 4 (IV). Thereafter, the focus lens 511 gradually decelerates and stops at the time $t=t_4$. The focus position of the focus lens 511 at this time is a stop position S near the target position P (V). The target position P is located within a depth of focus (depth $L_2$) of the focus lens 511 when the focus position is at the stop position S. Although FIG. 6 illustrates a case where the focus lens 511 stops after the passage of the focus position of the focus lens 511 through the target position P again, the focus lens 511 stops in some cases without the passage of the focus position of the focus lens 511 through the target position P again depending on the voice input timing of the user.

Figure 7:
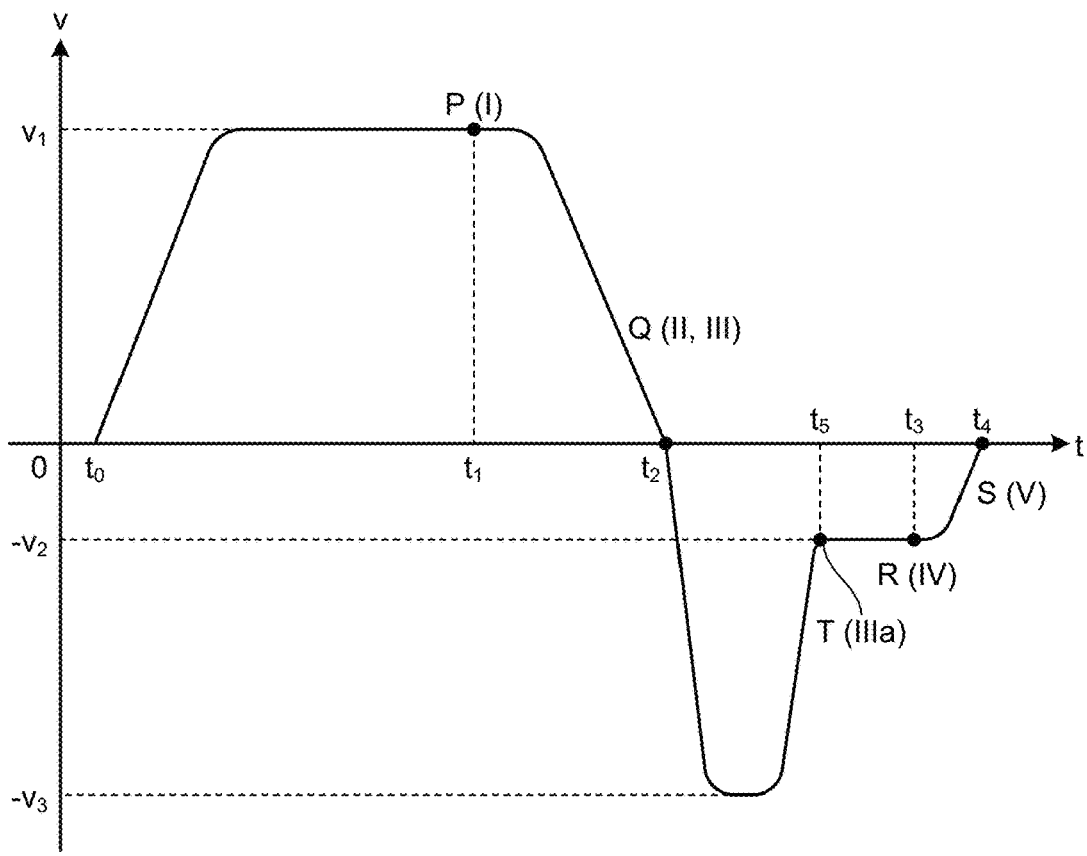
FIG. 7 is a diagram illustrating the relationship between time and velocity during focus operation in the second embodiment.

FIG. 7 is a diagram illustrating a relationship between the time and the velocity during the focus operation, specifically illustrating a relationship between the time and the velocity when the focus operation is started at the time $t=0$. The change from the start of operation of the focus lens 511 to the first stop is the same as in FIG. 3 (I to III). After this, the focus lens 511 moves at a constant velocity of the third velocity $v_3$, then decelerates, and starts the constant velocity movement at the second velocity $v_2$ at time $t_5$ at which the focus position passes through the return position T (IIIa). Thereafter, the user makes a voice input of "stop" again to the microphone 4 at time $t=t_3$ on which the focus position of the focus lens 511 passes through the return position R (IV), the focus lens 511 starts decelerating with a slight delay from the voice input, and stops at time $t=t_4$. The focus position of the focus lens 511 at this time is the stop position S (V).

FIG. 7 illustrates the case where the third velocity $v_3$ is higher than the first velocity $v_1$. This enables the focus lens 511 to quickly return to where the focus position is located in the vicinity of the target position P. The magnitude relationship between the first velocity $v_1$ and the third velocity $v_3$ is not limited to this case. The first velocity $v_1$ may be higher, or the first velocity $v_1$ and the third velocity $v_3$ may be equal.

The outline of the processes performed by the control apparatus according to the second embodiment is the similar to the outline of the processes described with reference to FIG. 5 in the first embodiment. However, in step S8, the control unit 66 generates a control signal to first reverse the direction of the focus lens 511, move the focus lens 511 for a predetermined time at a constant velocity of the third velocity $v_3$, and then decelerate to the second velocity $v_2$ to move at a constant velocity, and transmits the generated control signal to the control unit 5a.

According to the second embodiment described above, the focus adjustment by voice input may be achieved by a simple process with less load, similarly to the first embodiment.

Furthermore, according to the second embodiment, after the focus lens is stopped and reversed direction, the focus lens is moved at a constant velocity of a third velocity higher than the second velocity, and then the lens moves at the constant velocity of the decelerated second velocity. This enables the focus lens to be quickly returned to where the focus position of the focus lens reaches the vicinity of the target position, leading to the reduction of the adjustment time.

Note that it is also allowable to permit the user 101 to set and input via the input units 58 and 63 or the microphone 4 as to whether to move the focus lens at a constant velocity of the third velocity after reversal of the lens.

Second Modification

In a second modification of the second embodiment, after returning beyond the target position P at the third velocity $v_3$, the focus lens reverses the direction again and approaches the target position P. In the second modification, the direction of the second velocity $v_2$ is the same as the direction of the first velocity $v_1$.

Figure 8A:
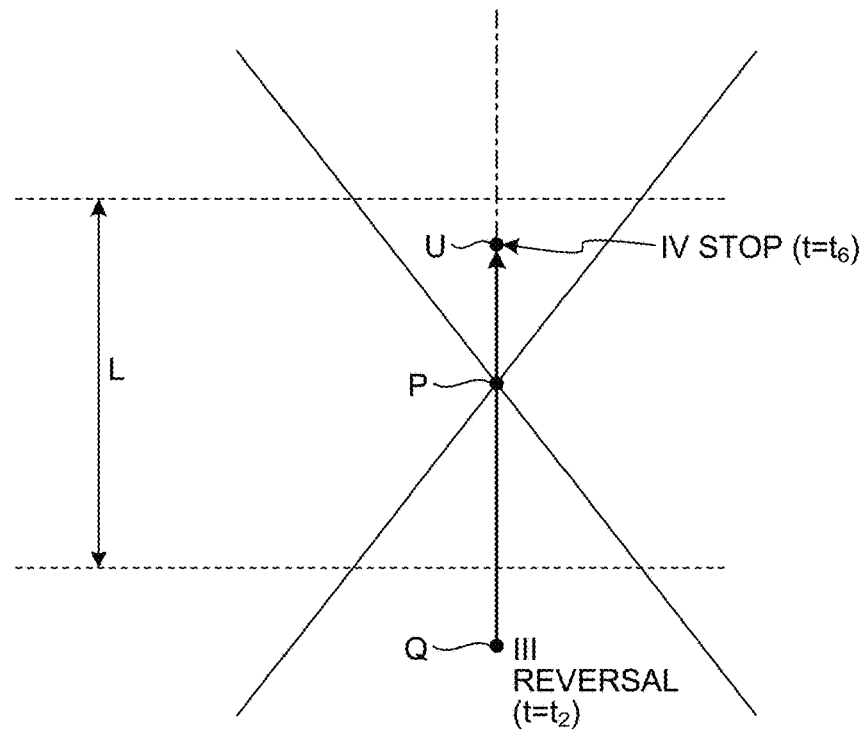
FIG. 8A is a diagram (part 1) schematically illustrating a movement of the focus position of the focus lens after the focus operation is stopped in a second modification of the second embodiment.
Figure 8B:
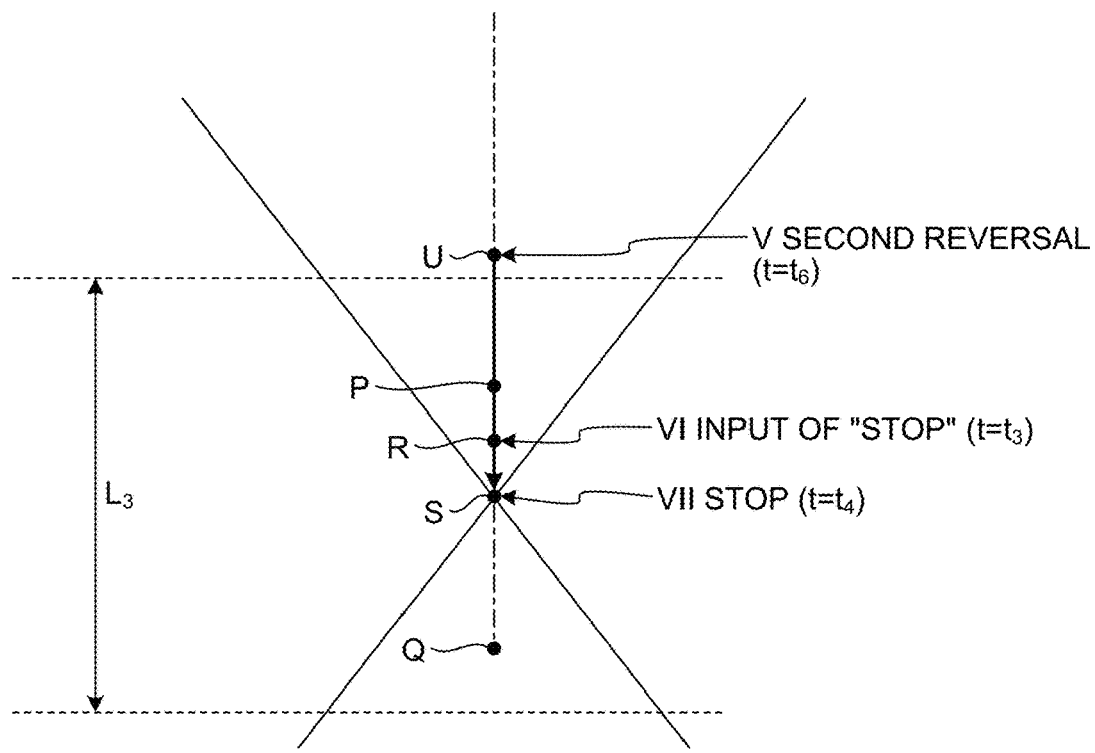
FIG. 8B is a diagram (part 2) schematically illustrating a movement of the focus position of the focus lens after the focus operation is stopped in the second modification of the second embodiment.

FIGS. 8A and 8B are diagrams schematically illustrating the movement of the focus position of the focus lens 511 after the focus operation is stopped. FIG. 8A illustrates the movement of the focus position of the focus lens 511 after the first reversal, and FIG. 8B illustrates the movement of the focus position of the focus lens 511 after the second reversal.

First, FIG. 8A will be described. Immediately after stopping at the time when the focus position is at the stop position Q at ($t=t_2$), the focus lens 511 reverses the direction and begins to return so that the focus position is directed toward the target position P (III). Thereafter, the focus lens 511 moves at a constant velocity of a third velocity $v_3$, which is higher than the second velocity $v_2$, and then stops where the focus position goes beyond the target position P. The focus position of the focus lens 511 at this time is the stop position U (IV).

Next, FIG. 8B will be described. Immediately after stopping at the time when the focus position is at the stop position U ($t=t_6$), the focus lens 511 performs second reversal and begins to return so that the focus position is directed toward the target position P (V). Thereafter, the focus lens 511 moves at a constant velocity of the second velocity $v_2$. Subsequently, at the time $t=t_3$ when the focus position of the focus lens 511 passes through the return position R, the user utters "stop" to input the utterance to the microphone 4 (VI). Thereafter, the focus lens 511 gradually decelerates and stops at the time $t=t_4$. The focus position of the focus lens 511 at this time is a stop position S near the target position P (VII). The target position P is located within a depth of focus (depth $L_3$) of the focus lens 511 when the focus position of the focus lens 511 is at the stop position S. Although FIG. 8B illustrates a case where the focus lens 511 stops after the passage of the focus position of the focus lens 511 through the target position P three times, the focus lens 511 stops in some cases without the passage of the focus position of the focus lens 511 through the target position P three times depending on the voice input timing of the user.

Figure 9:
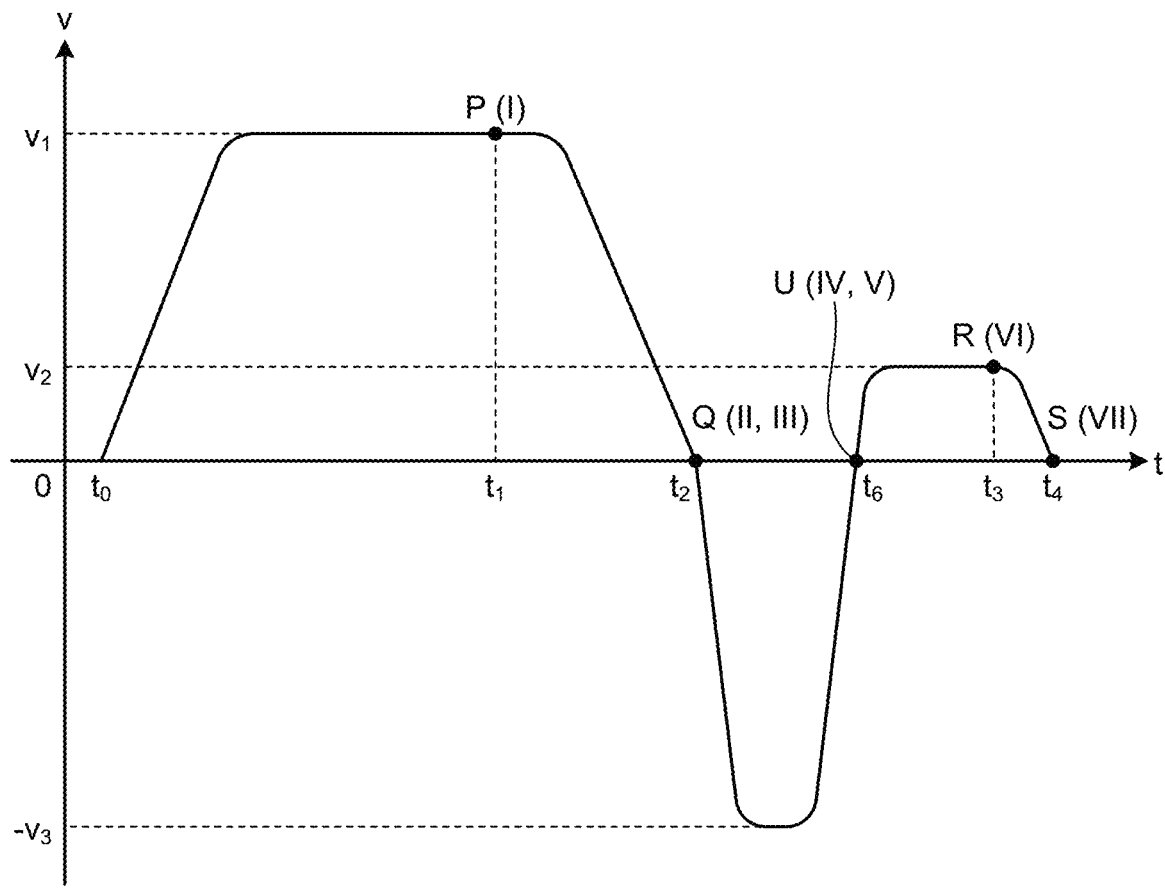
FIG. 9 is a diagram illustrating a relationship between time and velocity during focus operation in the second modification of the second embodiment.

FIG. 9 is a diagram illustrating a relationship between the time and the velocity during the focus operation, specifically illustrating a relationship between the time and the velocity when the focus operation is started at the time t=0. The change from the start of operation of the focus lens 511 to the first stop is the same as in FIG. 3 (I to III). Thereafter, the focus lens 511 moves at a constant velocity of the third velocity $v_3$, then decelerates so as to stop. The focus position of the focus lens 511 at this time is the stop position U beyond the target position P in the movement direction (IV). Subsequently, the focus lens 511 performs second reversal (V) and starts constant velocity movement at the second velocity $v_2$. Thereafter, the user makes a voice input of "stop" again to the microphone 4 at time $t=t_3$ on which the focus position of the focus lens 511 passes through the return position R (VI), the focus lens 511 starts decelerating with a slight delay from the voice input, and stops at time $t=t_4$. The focus position of the focus lens 511 at this time is the stop position S (VII).

According to the second modification of the second embodiment described above, since the direction of the first velocity and the direction of the second velocity are the same, the user may perform focusing while gradually reviewing the once experienced screen change, after deceleration of the focus lens.

Third Embodiment

In a third embodiment, when focus information extracted by the image processing unit satisfies a predetermined condition after start of the movement of the focus lens, the focus lens is controlled to move at a constant velocity of a second velocity that is lower than and in the same direction as the first velocity. The functional configuration of the medical observation system according to the third embodiment is the similar to that of the first embodiment.

Figure 10:
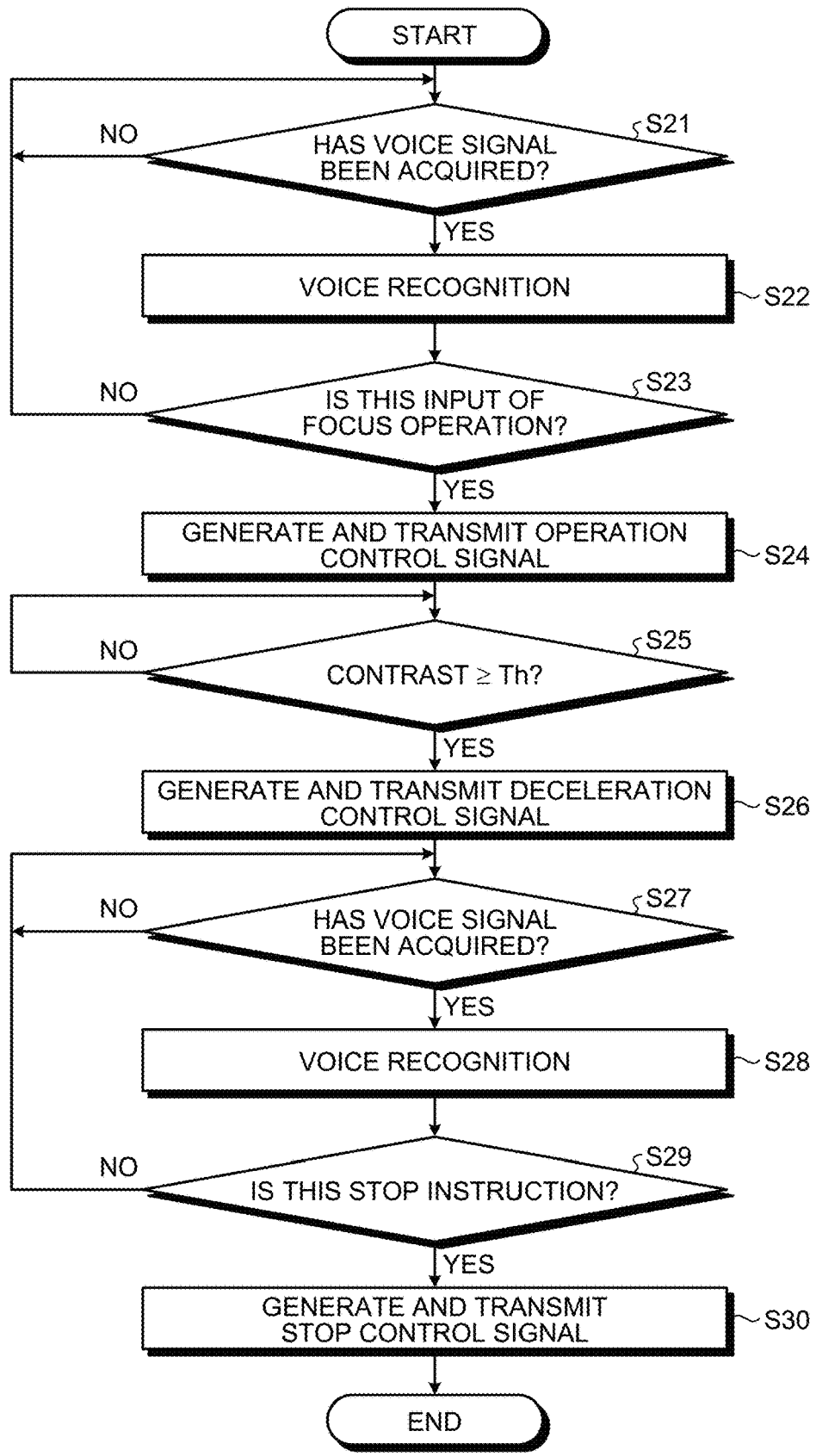
FIG. 10 is a flowchart illustrating an outline of processes performed by a control apparatus according to a third embodiment.

FIG. 10 is a flowchart illustrating an outline of processes performed by the control apparatus 6 according to the third embodiment. The initial processes of steps S21 to S24 respectively correspond to the processes of steps S1 to S4 described in the first embodiment.

Thereafter, the control unit 66 compares a contrast of the latest image detected by the image processing unit 62 with a predetermined threshold Th (step S25). The latest image referred to here is a most recent image acquired from the microscope apparatus 5. When it is determined, as a result of comparison, that the contrast of the latest image is the threshold Th or more (step S25: Yes), the control unit 66 generates a control signal (deceleration control signal) to decelerate to the second velocity $v_2$ without changing the direction of the velocity of the focus lens 511, and transmits the generated control signal to the control unit 5a (step S26).

Subsequent processes in steps S27 to S30 correspond respectively to steps S9 to S12 described in the first embodiment.

When the contrast of the latest image is lower than the threshold Th in step S25 (step S25: No), the control apparatus 6 repeats step S25.

Figure 11:
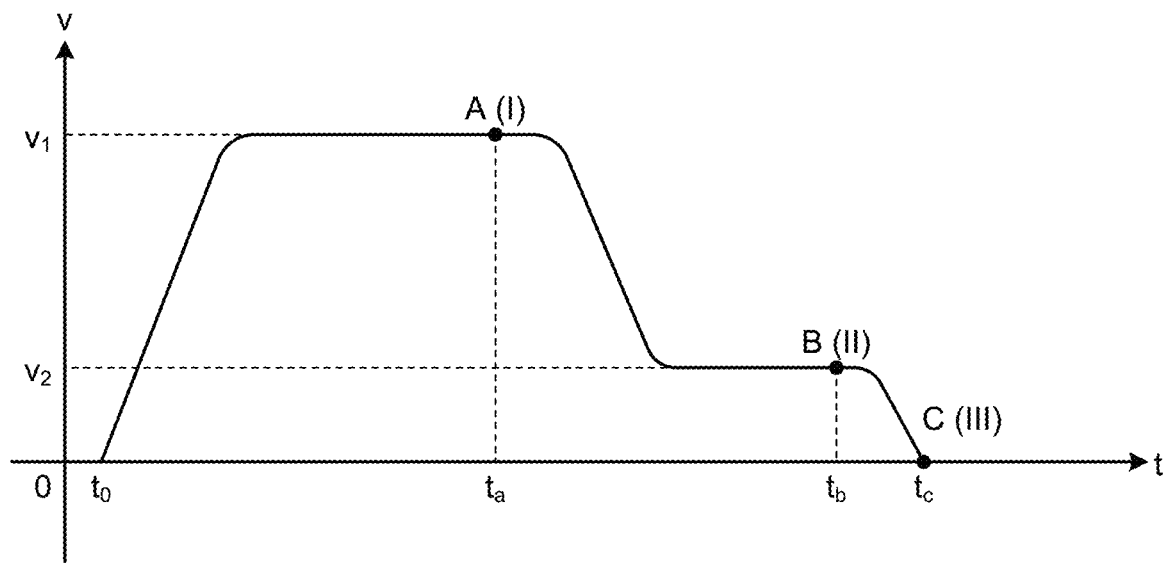
FIG. 11 is a diagram illustrating a relationship between time and velocity during focus operation in the third embodiment.

FIG. 11 is a diagram illustrating a relationship between the time and the velocity during the focus operation, specifically illustrating a relationship between the time and the velocity when the focus operation is started at the time t=0. The user makes a voice input of "focus in" or "focus out" to the microphone 4 at t=0, and then the focus lens 511 starts moving at time $t=t_0$ with a slight delay from the voice input, and eventually shifts to a constant velocity movement at a first velocity $v_1$. During this time, the image processing unit 62 sequentially detects the contrast of the image acquired from the microscope apparatus 5 as focus information and stores the information in the storage unit 67.

Thereafter, the contrast of the latest image becomes the threshold Th or more at time $t=t_a$ at which the focus lens 511 passes through a position A (I), and the control unit 66 outputs a control signal for decelerating to the second velocity $v_2$. After the focus lens 511 decelerates to the second velocity $v_2$, the focus lens 511 moves at the constant velocity. The user makes a voice input of "stop" to the microphone 4 at time $t=t_b$ on which the focus lens 511 passes through a position B (II), the focus lens 511 starts decelerating with a slight delay from the voice input, and stops at the stop position C at time $t=t_c$ (III).

Figure 12:
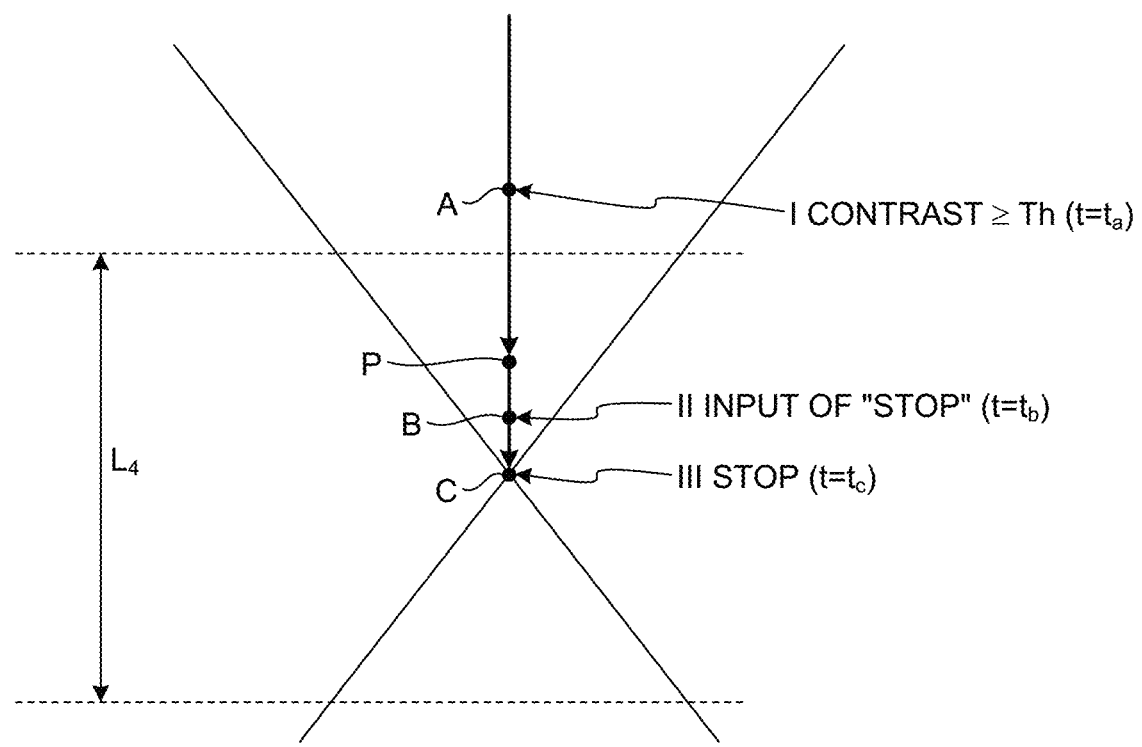
FIG. 12 is a diagram schematically illustrating the focus operation according to the third embodiment.

FIG. 12 is a diagram schematically illustrating the focus operation in the third embodiment. Positions A and B and stop position C illustrated in FIG. 12 correspond to positions A and B and stop position C illustrated in FIG. 11, respectively. As illustrated in FIG. 12, in the third embodiment, when the focus lens 511 is stopped in response to the voice input of the user, the focus position of the focus lens 511 approaches the target position P without reversing the direction of movement. The target position P is located within a depth of focus (depth $L_4$) of the focus lens 511 when the focus position is at the stop position C. Although FIG. 12 illustrates a case where the focus lens 511 stops after the focus position of the focus lens 511 goes beyond the target position P, the focus lens 511 stops in some cases before the focus position of the focus lens 511 reaches the target position P depending on the voice input timing of the user.

According to the third embodiment described above, the focus adjustment by voice input may be achieved by a simple process with less load, similarly to the first embodiment.

Furthermore, according to the third embodiment, since the velocity is reduced without performing the reversing operation, the time for focusing may be reduced.

In the third embodiment as well, the control unit 66 may set the second velocity $v_2$ based on the depth of focus according to the imaging conditions of the microscope apparatus 5 at the time of imaging, similarly to the first modification of the first embodiment.

Other Embodiments

Embodiments have been described hereinabove, however, the present disclosure is not intended to be limited to the above-described first to third embodiments. For example, the present disclosure is not limited to the focus operation, and it is possible to perform similar processes after stoppage of the various functional members by the user's voice input in the case of the zoom operation or the visual field movement.

Furthermore, the medical observation apparatus according to the present disclosure may be an endoscope or an endoscope equipped with an imaging device.

The present technology may also have the following configurations.

(1)
A control apparatus including:
an acquisition unit configured to acquire an operation instruction made by a voice input to an imaging device including: an optical system including a focus lens; and an image sensor; and
a controller configured to control the focus lens moving at a first velocity to stop movement when the operation instruction is an instruction to stop an operation of the focus lens, and control the focus lens to move at a second velocity lower than the first velocity.

(2)
The control apparatus according to (1), wherein the acquisition unit is configured to acquire, as the operation instruction, a voice signal generated by a microphone configured to receive a voice input.

(3)
The control apparatus according to (1) or (2), further including a voice recognition unit configured to recognize information contained in the operation instruction acquired by the acquisition unit.

(4)
The control apparatus according to any one of (1) to (3), wherein
the first and second velocities are constant velocities, and
the controller is configured to move the focus lens at a constant velocity of the second velocity.

(5)
The control apparatus according to any one of (1) to (4), wherein the controller is configured to stop operation of the focus lens when the controller has recognized a voice signal corresponding to an instruction to stop the operation of the focus lens while the focus lens is controlled to be moving at a constant velocity of the second velocity.

(6)
The control apparatus according to any one of (1) to (5), wherein the controller is configured to
control the focus lens to stop,
thereafter control the focus lens to move for a predetermined time at a third velocity that is opposite, in direction, to the first velocity and higher than the second velocity, and
then control the focus lens to move at the second velocity.

(7)
The control apparatus according to (6), wherein the third velocity is higher than the first velocity.

(8)
The control apparatus according to any one of (1) to (7), wherein the direction of the second velocity is opposite to the direction of the first velocity.

(9)
The control apparatus according to (6) or (7), wherein the direction of the second velocity is identical to the direction of the first velocity.

(10)
The control apparatus according to any one of (1) to (9), wherein the controller is configured to set the second velocity based on a depth of focus according to an imaging condition at a time of imaging performed by the image sensor.

(11)
The control apparatus according to (10), wherein the imaging condition is a magnification of the optical system.

(12)
The control apparatus according to (10), wherein the imaging condition is an aperture value of the optical system.

(13)
A medical observation system including:
an imaging device including
an optical system including a focus lens, and
an image sensor;
a microphone configured to receive a voice input of an operation instruction to the imaging device;
a control apparatus including
an acquisition unit configured to acquire a voice signal generated by the microphone,
a voice recognition unit configured to recognize information carried by the voice signal acquired by the acquisition unit, and
a controller configured to control the focus lens moving at a constant velocity of a first velocity to stop movement when the information carried by the voice signal recognized by the voice recognition unit is a focus lens operation stop instruction, and control the focus lens to move at a constant velocity of a second velocity lower than the first velocity; and
a display configured to display an image captured by the imaging device.

[Supplementary Note 1]

A control apparatus including:

an acquisition unit configured to acquire an image signal captured in imaging performed by an imaging device including: an optical system including a focus lens; and an imaging unit, the acquisition unit being configured to acquire an operation instruction made by a voice input to the imaging device;

an image processing unit configured to extract focus information of the image acquired by the acquisition unit, and a controller configured to control the focus lens to start movement when the operation instruction is a focus lens operation instruction at a first velocity, and control to the focus lens to move at a second velocity that is lower than and in a same direction of the first velocity when the focus information extracted by the image processing unit satisfies a predetermined condition.

[Supplementary Note 2]

The control apparatus according to Supplementary note 1, wherein the acquisition unit is configured to acquire, as the operation instruction, a voice signal generated by a microphone configured to receive a voice input.

[Supplementary Note 3]

The control apparatus according to Supplementary note 1 or 2, further including a voice recognition unit configured to recognize information contained in the operation instruction acquired by the acquisition unit.

[Supplementary Note 4]

The control apparatus according to any one of Supplementary notes 1 to 3, wherein the first and second velocities are constant velocities.

[Supplementary Note 5]

The control apparatus according to any one of Supplementary notes 1 to 4, wherein the controller is configured to stop operation of the focus lens when the controller has recognized a voice signal corresponding to an instruction to stop the operation of the focus lens while the focus lens is controlled to be moving at a constant velocity of the second velocity.

[Supplementary Note 6]

The control apparatus according to any one of Supplementary notes 1 to 5, wherein the focus information is contrast of an image.

[Supplementary Note 7]

The control apparatus according to any one of Supplementary notes 1 to 6, wherein the second velocity is a velocity capable of stopping within a depth of focus of the optical system.

[Supplementary Note 8]

The control apparatus according to any one of Supplementary notes 1 to 7, wherein the controller is configured to set the second velocity based on a depth of focus according to an imaging condition at a time of imaging performed by the image sensor.

[Supplementary Note 9]

The control apparatus according to Supplementary note 8, wherein the imaging condition is a magnification of the optical system.

[Supplementary Note 9]

The control apparatus according to Supplementary note 8, wherein the imaging condition is an aperture value of the optical system.

[Supplementary Note 11]

A medical observation system including:

an imaging device including an optical system including a focus lens, and an image sensor;

a control apparatus including an acquisition unit configured to acquire an image signal captured in imaging performed by the imaging device, and acquire an operation instruction made by a voice input to the imaging device, an image processing unit configured to extract focus information of the image acquired by the acquisition unit, and a controller configured to control the focus lens to start movement when the operation instruction is a focus lens operation instruction at a first velocity, and control to the focus lens to move at a second velocity that is lower than and in a same direction of the first velocity when the focus information extracted by the image processing unit satisfies a predetermined condition; and a display configured to display an image captured by the imaging device.

According to the present disclosure, focus adjustment by voice input may be achieved by a simple process with less load.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A control apparatus comprising:

acquisition circuitry configured to acquire an operation instruction made by a voice input to an imaging device including: an optical system including a focus lens; and an image sensor; and control circuitry configured to:

control the focus lens moving at a first velocity in a first direction to stop movement when the operation instruction is a first instruction to stop movement of the focus lens, and automatically control the focus lens to move at a second velocity lower than the first velocity in a second direction, opposite the first direction, in response to the first instruction to stop the operation of the focus lens, and stop the focus lens when the operation instruction is a second instruction to stop movement of the focus lens while the focus lens is moving at the second velocity.

2. The control apparatus according to claim 1, wherein the acquisition circuitry is configured to acquire, as the operation instruction, a voice signal generated by a microphone configured to receive a voice input.

3. The control apparatus according to claim 1, further comprising a voice recognition circuitry configured to recognize information contained in the operation instruction acquired by the acquisition circuitry.

4. The control apparatus according to claim 1, wherein the first and second velocities are constant velocities.

5. The control apparatus according to claim 1, wherein the control circuitry is configured to
control the focus lens to stop,
thereafter automatically control the focus lens to move for a predetermined time at a third velocity in the second direction and higher than the second velocity, and
then, after the predetermined time, automatically control the focus lens to move at the second velocity.

6. The control apparatus according to claim 5, wherein the third velocity is higher than the first velocity.

7. The control apparatus according to claim 1, wherein the control circuitry is configured to set the second velocity based on a depth of focus according to an imaging condition at a time of imaging performed by the image sensor.

8. The control apparatus according to claim 7, wherein the imaging condition is a magnification of the optical system.

9. The control apparatus according to claim 7, wherein the imaging condition is an aperture value of the optical system.

10. A medical observation system comprising:
an imaging device including
an optical system including a focus lens, and
an image sensor;
a control apparatus including
acquisition circuitry configured to acquire an operation instruction made by a voice input to the imaging device, and
control circuitry configured to
control the focus lens moving at a first velocity in a first direction to stop movement when the operation instruction is an instruction to stop movement of the focus lens,
automatically control the focus lens to move at a second velocity lower than the first velocity in a second direction, opposite the first direction, in response to the instruction to stop the operation of the focus lens, and
stop the focus lens when the operation instruction is a second instruction to stop movement of the focus lens while the focus lens is moving at the second velocity; and
a display configured to display an image captured by the imaging device.

11. The medical observation system according to claim 10, wherein the control circuitry is configured to control the focus lens to move in the first direction at the first velocity when the control circuitry has recognized a voice signal corresponding to an instruction to start focus operation.

12. The control apparatus according to claim 1, wherein the control circuitry is configured to control the focus lens to move in the first direction at the first velocity when the control circuitry has recognized a voice signal corresponding to an instruction to start focus operation.

13. The medical observation system according to claim 10, wherein the control circuitry is configured to set the second velocity based on a depth of focus according to an imaging condition at a time of imaging performed by the image sensor.

14. The medical observation system according to claim 13, wherein the imaging condition is a magnification of the optical system.

15. The medical observation system according to claim 13, wherein the imaging condition is an aperture value of the optical system.

* * * * *